U S008659762B2

(12) United States Patent
Bertholds et al.

(10) Patent No.: US 8,659,762 B2
(45) Date of Patent: Feb. 25, 2014

(54) OPTICAL MEASURING ELEMENT HAVING A SINGLE-PIECE STRUCTURE

(75) Inventors: Axel Bertholds, Verscio (CH); Pere Llosas, Minusio (CH); Simon Henein, Neuchâtel (CH)

(73) Assignee: Sensoptic SA, Losone (CH)

( * ) Notice: Subject to any disclaimer, the term of this patent is extended or adjusted under 35 U.S.C. 154(b) by 528 days.

(21) Appl. No.: 12/919,621

(22) PCT Filed: Mar. 18, 2009

(86) PCT No.: PCT/CH2009/000096
§ 371 (c)(1),
(2), (4) Date: Aug. 26, 2010

(87) PCT Pub. No.: WO2009/114955
PCT Pub. Date: Sep. 24, 2009

(65) Prior Publication Data
US 2010/0328675 A1    Dec. 30, 2010

Related U.S. Application Data

(60) Provisional application No. 61/043,439, filed on Apr. 9, 2008.

(30) Foreign Application Priority Data

Mar. 19, 2008 (CH) .......................... 418/08

(51) Int. Cl.
*G01B 9/02* (2006.01)
*G01B 11/02* (2006.01)
*G01N 21/25* (2006.01)
*G01L 1/24* (2006.01)

(52) U.S. Cl.
USPC .......... 356/498; 356/35.5; 356/480; 356/406; 356/419; 356/479; 356/497

(58) Field of Classification Search
USPC .................. 356/35.5, 480, 406, 419, 479, 497
See application file for complete search history.

(56) References Cited

U.S. PATENT DOCUMENTS

| 2008/0009750 | A1 | 1/2008 | Aeby | |
|---|---|---|---|---|
| 2008/0281209 | A1* | 11/2008 | Arkwright et al. | 600/478 |
| 2008/0294144 | A1* | 11/2008 | Leo et al. | 604/508 |

FOREIGN PATENT DOCUMENTS

WO    WO 2007/015139    2/2007

OTHER PUBLICATIONS

English translation of International Preliminary Examination Report on Patentability, issued May 10, 2010.

(Continued)

*Primary Examiner* — Tarifur Chowdhury
*Assistant Examiner* — Sunghee Y Gray
(74) *Attorney, Agent, or Firm* — Dority & Manning, P.A.

(57) ABSTRACT

An optical measuring element measures forces in at least one direction. The measuring element has a single-piece structure. There is an outside wall with notches introduced therein. Each notch defines parallel edges, and the notches define more or less elastically flexible zones in the structure and constitute the only connection between a first region and a second region of the structure. For optical distance measurements between the two regions of the structure, one or more optical fibers are each attached with one end thereof to a region of the structure such that reflective surfaces are located close to the ends. The reflective surfaces are firmly connected to another region. The optical fibers are disposed on the outside wall.

20 Claims, 4 Drawing Sheets

(56) References Cited

OTHER PUBLICATIONS

International Search Report on Patentability, issued May 20, 2009.
Peirs J. et al: "A micro optical force sensor for force feedback during minimally invasive robotic surgery" Sensors and Actuatorsa, Elsevier Sequoia S.A., Lausanne, CH, vol. 115, No. 2-3, Sep. 21, 2004, pp. 447-455.

* cited by examiner

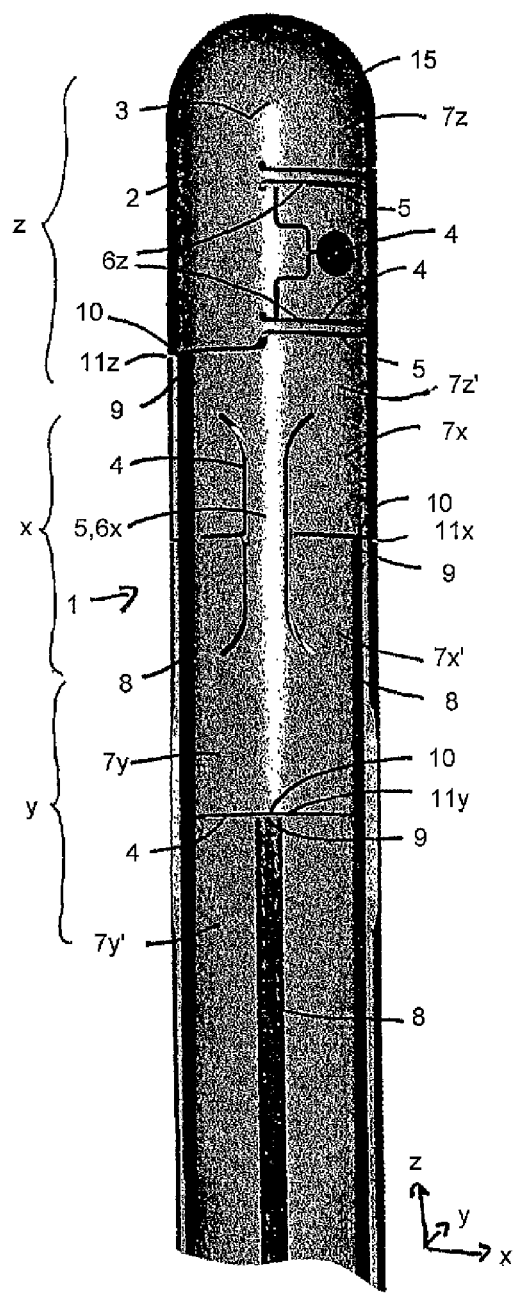
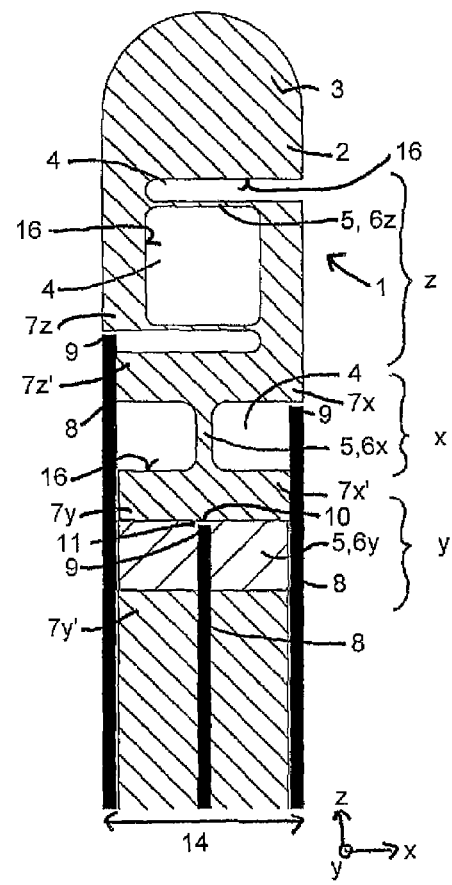
Fig. 1
Fig. 2

OPTICAL MEASURING ELEMENT HAVING A SINGLE-PIECE STRUCTURE

CROSS-REFERENCE TO RELATED APPLICATIONS

This application claims priority to International Application Serial No. PCT/CH2009/000096 filed Mar. 18, 2009, which claims priority to Swiss Application No. CH 418/08 filed Mar. 19, 2008, and U.S. Provisional Patent Application Ser. No. 61/043,439, filed Apr. 9, 2008.

TECHNICAL FIELD

The invention relates to an optical measuring element for measuring forces in at least one direction wherein said measuring element has a single-piece structure comprising an outside wall and notches introduced therein. The notches define one or more elastically flexible zones within the structure which constitute the only connection between a first and a second region of the structure. For optical distance measurements between the two regions of the structure, one or more optical fibers are each attached with one end thereof to a region of the structure such that close to the ends reflective surfaces are located which are firmly connected to another region.

BACKGROUND

Optical force measuring elements provide the advantage over other force measuring elements such as those based on DMS in that optical force measuring elements are free of electrical lines and connections. This is particularly advantageous if they are used in environments where electromagnetic disturbances can be expected. Furthermore, the possibility of miniaturization is limited for such measuring elements based on DMS because of the electrical contacts. Optical force measuring elements are useful for medical purposes, especially for invasive applications. Other fields of use include for example robotics technology. The differentials between the optically measured distances are proportional to the acting forces that deform the structure.

WO 2007/015139 describes a catheter with a sensor tip having an optical force measuring element attached to the end thereof. This sensor tip can be placed in a human organ, for example in a heart, at the wall thereof where it determines the three-dimensional force acting on the sensor tip that is generated by the organ wall. In this way, a so called "mapping" of vessels and organs can be performed.

The publication by J. Peirs, J. Clijnen, P. Herijgers, D. Reynaerts, H. Van Brussel, B. Corteville and S. Boone "Design of an Optical Force Sensor for Force Feedback during Minimally Invasive Robotic Surgery" describes an optical sensor which can be used for example for the application mentioned above. It describes an elastic cylindrical outer structure in the center of which three optical fibers with three fiber ends have been axially inserted. These measure the distance to a fixed end which approaches the fiber ends depending on the action of a force onto the upper part of the structure. A disadvantage of this sensor is the limited possibility of miniaturization. In addition, the measurements of the forces in the three x, y, and z directions are always linked to each other.

US 2008/0009750 suggests a catheter tip incorporating the structure mentioned in the beginning. It is identical to the structure already described in the publication by Peirs et al. It consists of a tube cut into a flexible structure by radially disposed notches in the central region. The flexible structure has a plurality of columns that are alternatingly connected to an upper and a lower annulus wherein each adjacent pair of columns is connected to each other by two flexible bridges. In the lower annulus, optical fibers are arranged in openings that can measure the distance to the lower ends of the columns attached at the upper end or to the bridges to thereby deduce the forces acting on the upper annulus.

Since all notches and thus all edges of the columns and the elastic bridges extend radially with respect to the tube axis, the columns at the tube outer wall are thicker than those at the tube inner wall, and the bridges are softer at the tube outer wall than those at the tube inner wall because the latter are shorter. For this reason, the tube must be provided with a thin wall thickness with respect to the tube outer diameter, about 1:10, to ensure flexibility of the elastic bridges. The dimensions mentioned of 0.5 mm wall thickness and 5 mm tube diameter must not be under-run because otherwise the structure would become too unstable. However, for many applications, for example also for catheters, smaller sensors are demanded.

Another disadvantage of this structure is that due to the spiral construction of the structure, a force acting both in the axial and in the radial direction onto the structure always causes torsion. This torsion as a consequence of the structure makes it difficult to calculate the three-dimensionally acting forces from the distance measurements obtained. In particular, it is not obvious in the catheter described as to how a force acting on the catheter tip is transmitted to the tube since no connection to the catheter tip is provided except via the outside wall. Therefore, an axial load would scarcely be transmitted to the measuring element.

OBJECTS AND SUMMARY OF THE PRESENT INVENTION

It is an object of the present invention to suggest a measuring element in accordance with the sensor described herein that can be manufactured to be smaller and more simple and that provides for a more reliable inference of the acting forces from the measured data. In addition, it shall be possible to measure the forces in x, y, and z direction independently.

The idea underlying the invention is that in the measuring element according to the invention the optical fibers are arranged at the outside wall, i.e., at the outer surface of the structure. On the one hand, they can be attached more easily in this way since they can be installed and/or fixed from outside. But most notably, in this way the structure does not necessarily require a central bore so that the structure can be made more robust, more compact, and smaller. Additionally, the idea underlying the present invention is that each notch consists of parallel edges. Because of these flat notches, the structure is not necessarily required to be tubular but can be made solid wherein a central bore can be provided for all intents and purposes. For miniaturized modifications, this bore should at a maximum comprise about half of the diameter of the total structure for the residual material still to have the required strength. The diameter of a structure according to the invention is less than half of the diameter of a structure according to the prior art.

Additionally, in a preferred embodiment, the structure becomes even more precise as a measuring element due to the generation of independent elastically flexible zones which are each deformable only in one direction x, y, or z because in this case the individual force components can be measured in a decoupled manner.

BRIEF DESCRIPTION OF THE DRAWINGS

In the following, the invention will be explained in more detail with respect to the drawings in which FIG. 1 is a photographic representation of a measuring element according to the invention;

FIG. 2 is a schematic representation of a sensor of the invention according to FIG. 1 in longitudinal cross-sectional view in the z-x plane;

WAYS OF EMBODYING THE PRESENT INVENTION

Figure 3:
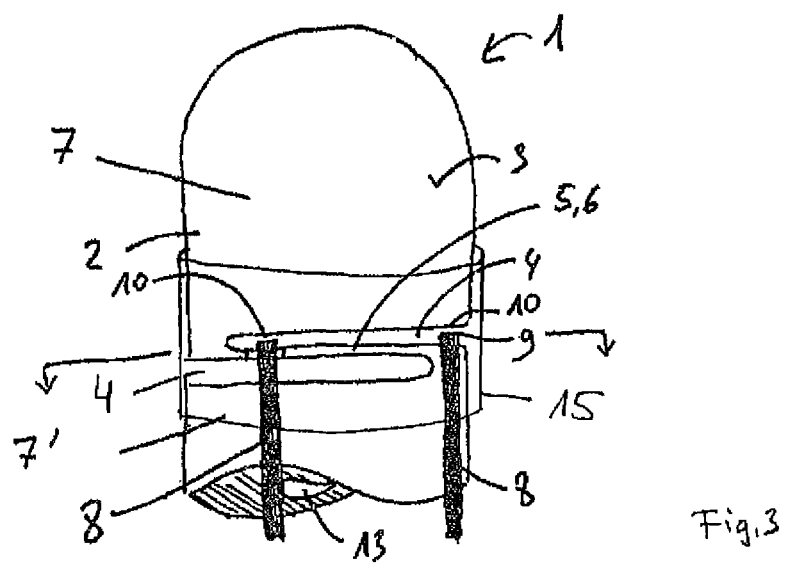
FIG. 3 is a schematic representation of a sensor of the invention in an alternative, coupled embodiment.

FIG. 1 shows a perspective photographic representation of a measuring element according to the invention. The optical measuring element 1 shown is useful for the measurement of forces in three directions x, y, and z wherein z extends in the axial direction of the measuring element, and x and y extend perpendicular thereto in radial direction.

FIG. 2 shows the same measuring element as FIG. 1 although in a schematic, simplified representation. In this representation any nonessential material in the structure has been omitted so that the mode of operation is more easily understood. Particularly evident are the connections which subdivide the structure into regions. Thus, FIG. 2 can be considered as equivalent to FIG. 1 only that the proportions in FIG. 1 are drawn according to reality whereas in FIG. 2 they are not.

The measuring element 1 comprises a single-piece structure 2 with an outer surface, the outside wall 3, and with notches 4 introduced into the structure 2. These notches 4 define a number of elastically flexible zones 5 in the structure 2 that represent the only connections 6x, 6y, and 6z each between a first region 7x and a second region 7x', between the regions 7y and 7y', and between 7z and 7z', respectively, of the structure 2. Preferably, the flexible zones 5 are formed in all variations as thin bridges. In particular, the measuring element 1 has a rounded end suitable to absorb and to transmit the force to be measured three-dimensionally into the individual regions 7.

In this embodiment, as shown in FIG. 2 for example, the region 7z' is identical to 7x, and 7x' is identical to 7y. Thus, this measuring element has four regions 7 separated by connections 6.

Figure 6:
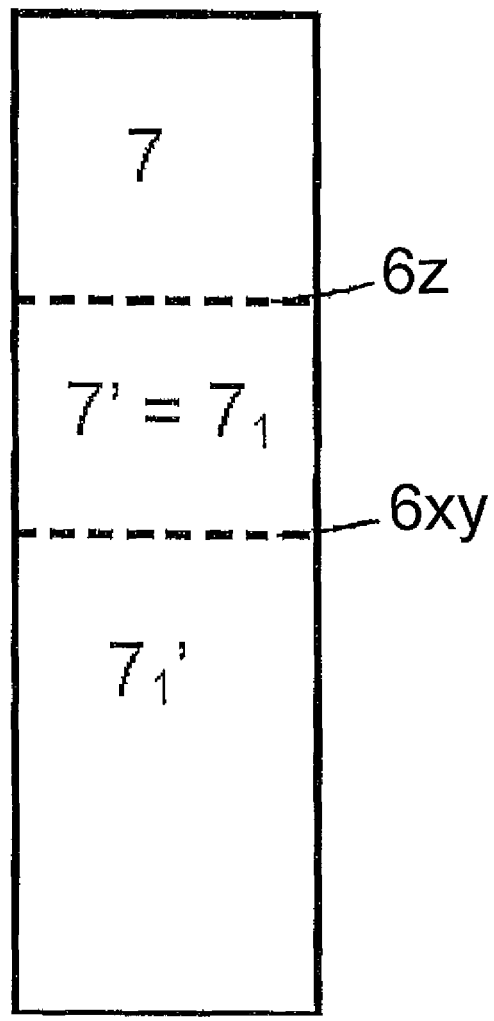
FIG. 6 shows a schematic representation of a section of a sensor of the invention in an alternative embodiment which is partially coupled.

Accordingly, simpler measuring elements 1 comprise notches 4 having only one connection 6 which can consist of several elastically flexible zones 5. These notches 4 divide the measuring element 1 into exactly two regions 7 and 7'. Thus, alternatively, as schematically shown in FIG. 6, the notches 4 can also divide the measuring element 1 into three regions 7, 7'=7$_1$ and 7$_1$' by means of two connections 6z, 6xy. In this embodiment, one connection 6 can allow for a flexible zone in more than one direction.

Between each two regions 7, 7' there is a gap distance 11 defined by notches 4 that varies if a force acts onto the sensor tip. If a force acts from the z direction the gap distance 11z varies, and the same applies for forces acting from the x and y directions.

For optical distance measurements between each two regions 7, 7' of the structure 2 an optical fiber 8 is attached to the second of these regions 7' with one end 9 to the structure 2 such that opposite to this end 9, at the first region 7, a reflective surface 10 is located that is firmly attached to this first region 7. During a measurement, light emitted from this optical fiber 8 is reflected at the reflective surface 10 whereafter it re-enters the optical fiber 8. An analytical instrument connected to the optical fiber can infer the gap distance 11 and, thus, the force that acts on the measuring element 1 from the information obtained.

According to the invention, these optical fibers 8 are attached to the outside wall or the outer surface 3 of the measuring element 1. In contrast to the prior art where the optical fibers are installed on the inside of the tubular structure, the present arrangement can be fabricated more easily, more cost-effectively and more precisely. According to the invention, openings to the outside wall 3 are located at the structure 2 into which the optical fibers can be introduced. The optical fibers 8 can then be introduced in the openings of the structure 2 from the outside wall 3 or from the lower end. The opening to the outside wall 3 is particularly important for the attachment of the optical fibers 8 at the structure 2. Thereby, this holding and firmly attaching of the optical fibers 8 at the outside wall 3 is more simple and does not require an additional central element in which the optical fibers must first be installed before this element is assembled with the structure to form the measuring element. Furthermore, with this type of construction the diameter of the measuring element 1 can be markedly reduced, i.e. for measurements of up to 5 N to 2.5 mm or less, which is very important especially for medical applications. For diameters of 1.7 to 2 mm it is possible to measure forces of 0.01 to 1 N without any risk of damage to the structure.

Another advantage can be achieved if—as in the arrangements shown—all notches 4 penetrate the whole structure 2 up to the opposite outside wall 3. Furthermore, they are made by incisions that each separately define parallel edges 16. For this reason it is no longer necessary to rotate the measuring element during fabrication, which can be done more cheaply while defining more precise cuts.

In contrast to what is described above, the notches 4 of the known prior art penetrate the tubular structure only radially causing the fabrication to be more expensive.

Usually, the notches 4 are manufactured by wire cut EDM (wire EDM; EDM: electrical discharge machining, spark erosion) whereby notches 4 with a width down to 0.05 mm are achieved.

According to the invention, in an measuring element 1 there are used at least as many optical fibers 8 as directions are measured. Thus, in a measuring element 1 with only one component to be measured, the use of only one optical fiber 8 is sufficient. While for two components, at least two optical fibers 8, and for three components at least three optical fibers 8 have to be disposed at the structure. Each optical fiber measures the distance between two adjacent regions 7 of the single-piece structure 2. If more than the necessary number of optical fibers 8 are operating, errors may be minimized consequently by utilizing known mathematical methods.

The connections 6 in FIGS. 1 and 2 between two adjacent structures function independently of each other, and each allows for deformations in one direction x, y, and z only. Therefore, by three connections, the structure is subdivided into four regions 7 arranged in series wherein a first connection only allows for deformations in the x direction, a second connection only allows for deformations in the y direction, and a third connection only allows for deformations in the z direction.

Accordingly, three optical fibers 8 are arranged at the structure, each of which is able to measure the spacing of a gap distance 11 between two different regions 7. In this arrangement, the forces acting in the three directions are decoupled from each other.

Figure 4:
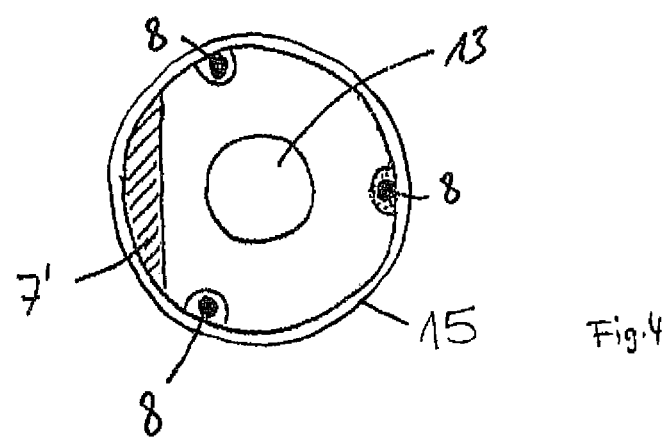
FIG. 4 shows a cross-section of the representation according to FIG. 3.

FIG. 3 shows a structure 2 in which the forces are not decoupled. FIG. 4 shows a cross-section through FIG. 3.

In this structure 2, two notches 4 have been introduced that define an elastically flexible zone 5 and thus a connection 6. This connection 6 allows for deformations in all three directions x, y, and z. Further notches 4 can be manufactured analogously at a structure such that the connections 6 generated thereby allow for deformations in two of the directions x, y, and z.

The structure shown in FIG. 3 is subdivided by a connection in two regions 7. Three optical fibers 8 at different locations measure the distance between these regions 7, 7'. They are arranged approximately uniformly at the outside wall 3. Two of the optical fibers 8', 8" pass through the connection at which they are not attached themselves without contact.

In other configurations there are at least as many optical fibers 8 as directions to be measured between two adjacent regions 7.

As described in FIGS. 1 and 2, the optical fibers are suitably attached to measure during a measurement the distance to the opposite, reflective surface that is firmly attached to the adjacent region 7. An analytical device calculates the forces that have acted on the structure 2 in the x, y, and z directions from the distance measurements obtained. In this FIG. 3 arrangement, the forces are coupled to each other. Unlike the arrangement shown in FIG. 1, this FIG. 3 arrangement may be less precise, but on the other hand the FIG. 3 structure is much shorter, namely about 5 mm in length.

For uses of the measuring element for invasive and minimally invasive medical purposes, a short length is very important.

Such short measuring elements can be introduced through catheters with small bending radius. These are for example required for cardio-vascular applications since the path within the heart to the veins follows narrow turns.

Additionally, as demonstrated in FIGS. 3 and 4, the structure may be a solid body or a hollow body having a continuous or discontinuous central cavity 13. A cavity 13 of this type may also be present in any other of the structures 2 according to the invention. For catheter applications continuous cavities 13 are important for the passage of small electrical leads and/or a fine tube for liquids. Furthermore, the cavity 13 can be used to accommodate leads for visual devices such as cables for a camera or optical fiber bundles for endoscopic uses.

Figure 5:
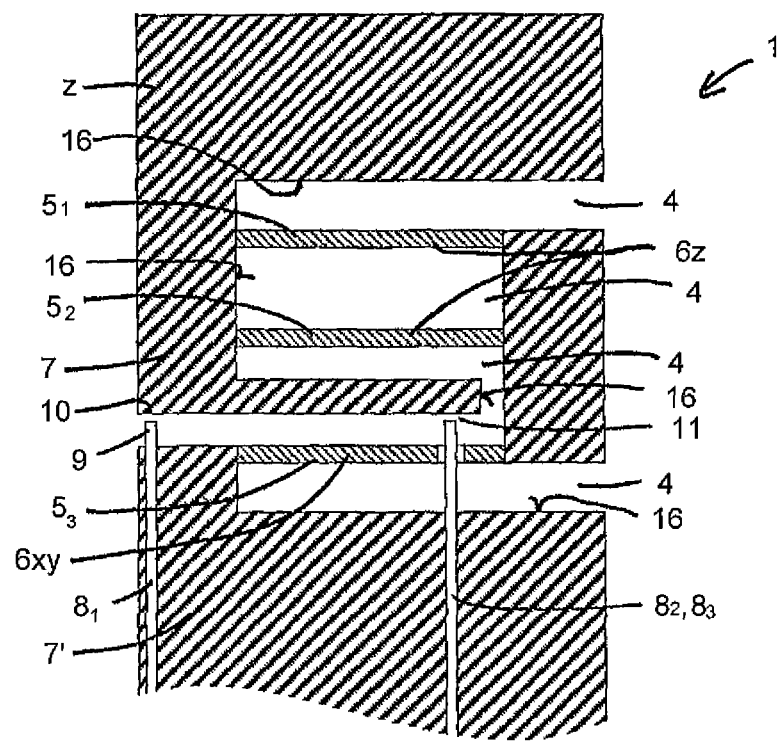
FIG. 5 shows a schematic representation of a sensor of the invention in an alternative embodiment which is partially coupled.

Another structure according to the invention is shown schematically in FIG. 5. This structure is a semi-decoupled system. The two elastically flexible zones $5_1$ and $5_2$ form a connection $6_z$ allowing a motion in the z direction while the elastically flexible zone $5_3$ is a connection $6_{x,y}$ for the x and y directions. In this case no complete decoupling is achieved, and therefore errors must be corrected by calculation. Of course, like all structures described herein the structure 2 is formed as a single-piece, and the different hatchings within the structure merely serve to illustrate its mode of operation. The optical fibers $8_2$ and $8_3$ are passed through the connection 6 of the elastically flexible zone $5_3$ without contact.

An advantage of the arrangements shown in FIGS. 3 and 5 is that the notches 4 run only in two dimensions, for example (x, z), whereby they can be fabricated in one step. The notches 4 in FIG. 1 must be machined in two steps from two different directions (x, z) and (y, z). However, the notches of the prior art must be made from all directions while the structure is rotated.

The optical distance measurements may be in particular carried out using an photometric measurement principle or using intensity measurements. For this purpose, each optical fiber 8 in all structures may especially consist of a pair of optical fibers. Interferometric measurements, particularly white light interferometry, have proven to be much more precise than intensity measurements.

Furthermore, the structure may be surrounded at least in the region of the notches 4 by a membrane sheath 15 for sealing purposes. This prevents liquids or other contaminants from entering and is particularly required if the structure is used for medical purposes, for example. Preferably, this membrane sheath may consist of rubber, Teflon, or silicone. If the structure includes a central cavity 13 the inner edge thereof is also sealed, for example by a Teflon tube.

An overload protection prevents the ends of the optical fibers 9 from contacting the opposite reflective surfaces in case of an overload and/or prevents an irreversible deformation of the structure. An overload protection of this type required by the construction can consist of a stop between adjacent regions 7 which prevents in case of a high load one end of an optical fiber 9 from contacting the structure 2. Alternatively, the optical fiber 8 can also be slightly offset backwards to avoid a collision. Advantageously, the optical fiber 8 is not mounted exactly at the site where the variation of the gap distance 11 under an acting force will be greatest and where, accordingly, the gap distance can be expected to disappear in case of an overload but instead adjacent thereto, laterally displaced where a minimal distance will always be left.

The structure can be made from any electrically conductive material that can be processed easily and precisely such as for example titanium. An alternative material in this respect is conductive ceramics or a semiconductor material, in particular silicon.

LIST OF REFERENCE NUMERALS 1 optical measuring element
2 single-piece structure
3 outside wall, outer surface
4 notch
5 elastically flexible zones
6 connection
7 region
8 optical fiber
9 end of optical fiber
10 reflective faces
11 gap distance
12 directions
13 central cavity
14 diameter
15 membrane sheath
16 edge of a notch

The invention claimed is:
1. An optical measuring element for measuring forces in at least one direction wherein said measuring element comprises a single-piece structure that elongates in a longitudinal direction with an outside wall and with at least two notches introduced therein wherein said notches define an elastically flexible zone in the structure being the only connection between a first region and a second region of the structure spaced apart, and wherein for optical distance measurements between the two regions of the structure at least one optical fiber is attached with one end thereof to one of the regions of the structure such that close to the end of said optical fiber a reflective surface is located which is firmly connected to the other of the two regions, wherein the optical fiber is disposed at the outside wall and that each notch consists of parallel edges within the structure in way that the edges the surrounding the notch within the structure are defined by parallel straight lines within the structure, all such lines being parallel to themselves.

2. A measuring element according to claim 1 wherein each notch penetrates the whole structure to the outside wall.

3. A measuring element according to claim 1, further comprising at least a second optical fiber disposed for optical distance measurements between two distinct regions of the structure.

4. A measuring element according to claim 3 wherein the structure is subdivided by several connections having elastically flexible zones in at least three distinct regions.

5. A measuring element according to claim 4 wherein between each two adjacent regions at least one optical fiber for optical distance measurements is disposed at the structure.

6. A measuring element according to claim 4 wherein each connection between two adjacent structures is formed by an elastically flexible zone that allows for deformations in only one of the directions x, y, and z.

7. A measuring element according to claim 6 wherein the structure is subdivided by three connections into four regions arranged in series wherein a first connection is formed by an elastically flexible zone that allows for deformations in the x direction only, a second connection is formed by an elastically flexible zone that allows for deformations in the y direction only, and a third connection is formed by an elastically flexible zone that allows for deformations in the z direction only.

8. A measuring element according to claim 1, wherein at least one of the connections is formed by an elastically flexible zone that will allow for deformations in at least two of the directions x, y, and z.

9. A measuring element according to claim 8 wherein at least two optical fibers are arranged for optical distance measurements between the two regions of the structure.

10. A measuring element according to claim 1, wherein the structure is a hollow body having a central cavity.

11. A measuring element according to claim 1, wherein the structure has a diameter of less than 2.5 mm.

12. A measuring element according to claim 1, wherein the optical distance measurement can be measured by an interferometric measurement principle.

13. A measuring element according to claim 1, wherein each optical fiber consists of a pair of optical fibers for photometric measurements.

14. A measuring element according to claim 1, wherein the structure is surrounded at least in the region of the connections by a membrane sheath for sealing.

15. A measuring element according to claim 1, further comprising an overload protection that prevents the end of the optical fiber from contacting the opposite reflective face in case of an overload and/or prevents an irreversible deformation of the structure.

16. A measuring element according to claim 1, wherein the structure is made of a conductive ceramic or of a semiconductor material.

17. The use of a measuring element according claim 1, wherein such use is for invasive and/or minimally invasive medical purposes.

18. The use of the measuring element according to claim 1, wherein the optical distance measurement is carried out using an interferometric measurement principle.

19. A measuring element according to claim 1, wherein the structure is made of silicon.

20. The use of the measuring element according to claim 1, wherein the optical distance measurement is carried out using white light interferometry.

* * * * *